United States Patent [19]

Hillyard et al.

[11] Patent Number: 4,894,347

[45] Date of Patent: Jan. 16, 1990

[54] ERYTHROCYTE AGGLUTINATION ASSAY

[75] Inventors: Carmel J. Hillyard, Brisbane; Dennis B. Rylatt, Rosalie; Bruce E. Kemp, Kew; Peter G. Bundesen, Fig Tree Pocket, all of Australia

[73] Assignee: Agen Limited, Australia

[21] Appl. No.: 143,343

[22] Filed: Jan. 13, 1988

Related U.S. Application Data

[63] Continuation-in-part of Ser. No. 111,313, Oct. 22, 1989.

[30] Foreign Application Priority Data

Sep. 17, 1987 [AU] Australia .................................. PI4400

[51] Int. Cl.$^4$ .......................................... G01N 33/541
[52] U.S. Cl. ..................................... 436/540; 436/501; 436/519; 422/61; 530/387
[58] Field of Search ................... 530/387, 389; 422/61; 436/519, 520, 540, 501

[56] References Cited

U.S. PATENT DOCUMENTS

| 4,433,059 | 2/1984 | Chang et al. | 436/520 |
| 4,470,925 | 9/1984 | Auditore-Hargreaves | |
| 4,529,712 | 7/1985 | Jou et al. | 436/519 |
| 4,578,360 | 3/1986 | Smith | 436/500 |
| 4,594,327 | 6/1986 | Zuk | 435/805 |
| 4,829,011 | 5/1989 | Gibbons | 436/512 |

Primary Examiner—Barry S. Richman
Assistant Examiner—Lyle Alfandary-Alexander
Attorney, Agent, or Firm—Iver P. Cooper

[57] ABSTRACT

In an erythrocyte agglutination assay, the agglutination reagent comprises at least one erythrocyte binding molecule coupled to at least one specific analyte binding molecule wherein the erythrocyte binding molecule does not cause agglutination when incubated with erythrocytes in the absence of analyte. Preferably, the erythrocytes are endogenous to the blood sample to be tested, that is, a whole blood sample is assayed. Mixtures of conjugates and conjugates of analyte analogues with erythrocyte binding molecules may also be used as agglutination reagents. The reagents and their use in direct or indirect assays is disclosed.

5 Claims, 4 Drawing Sheets

KEY: REAGENT — ANTIGEN — PATIENT Ab

NEGATIVE / NO AGGLUTINATION

POSITIVE / AGGLUTINATION

KEY

REAGENT     ANTIGEN     ANTIBODY

NEGATIVE

+  ▷

AGGLUTINATION

POSITIVE

+  ▷

INHIBITION

REAGENT

ANTIGEN

ANTIBODY 2

NEGATIVE

NO AGGLUTINATION

POSITIVE

AGGLUTINATION

ERYTHROCYTE AGGLUTINATION ASSAY

CROSS REFERENCE TO RELATED APPLICATIONS

This application is a continuation-in-part of Ser. No. 111,313, filed Oct. 22, 1987, now pending, from which priority is claimed under 35 U.S.C. 120. Priority under 35 U.S.C. 119 is claimed from Australian provisional application PI 4400 filed Sept. 17, 1987. The text of all priority applications is hereby incorporated by reference into the present application.

BACKGROUND OF THE INVENTION

1. Field of the Invention

The present invention relates to a reagent and a method for detecting an antigen, antibody or other analyte in human or animal blood by erythrocyte agglutination. The invention also concerns a kit containing the reagent and processes of preparation of the reagents.

2. Information Disclosure Statement

Assaying blood samples for a particular antigen or antibody has traditionally involved the step of separating the cellular components from the serum components of the blood by centrifugation and/or clotting, prior to assay.

This presents several potential problems. Firstly, such an assay is not suited to testing being conducted under field conditions. In many veterinary situations a quick test in the field is more desirable than the alternative of transporting samples to laboratories for separation and assay. Also, veterinary surgeons who do not have access to a centrifuge frequently need to assay blood samples for the presence of infectious agents such as heartworm. Further, assays being used for the detection of diseases in Third World countries present a situation where simplicity and low cost are of the essence.

Secondly, in certain pathologic conditions, separation of the blood samples becomes difficult. Blood taken from patients suffering conditions such as Waldenstrom's macroglobulinemia is difficult to separate into serum and cell fractions making an assay which can be conducted on whole blood highly desirable.

Thirdly, blood samples are often used for testing for the presence of highly contagious and potentially dangerous disease states. In these cases it is preferable that as little handling and processing of the samples as possible is undertaken in order to minimize the risk to personnel conducting the assay. Further, certain conditions make the provision of over-the-counter finger-prick assays highly desirable. Such assays must necessarily be suited to performance on whole blood.

Immunoassays have revolutionized human diagnostic and veterinary medicine since the introduction of techniques such as the radioimmunoassay, first reported by Yalow and Berson (1959) Nature 184, 1648, and the enzyme immunoassay or EIA which was first reported by Engvall and Perlman (1971) Immunochem 8, 871 and Van Weeman and Schuurs (1971) FEBS Letters 15, 232.

Whilst such assays are based on antibody-antigen interactions the detection systems utilized are usually complex. The reagents used are generally enzyme or radiolabelled antigens, antibodies or complexes thereof which require either incubation with specific substrates and measurement of a color end-point either visually or by means of a colorimeter or measurement of radioactive decay with radiation counters to detect the presence of the analyte being tested. These assays also involve several washing steps. Most immunoassays for the detection of analytes in blood are currently of this nature. Thus, whilst these assays are sensitive, they are lengthy and involved procedures which may require expensive instrumentation, for detection of the analyte under test.

An alternative to these assays is provided by immunoassays of the type described by Gupta, et al., (1985) Journal of Immunological Methods 30 177-187. These are immunoassays in which erythrocytes and anti-erythrocyte antibodies are used in the indicator system. In these assays exogenous erythrocytes such as sheep erythrocytes are used.

In recent years it has been possible to attach antibodies to latex beads, thus providing a rapid agglutination assay. This, however, still entails the separation of the serum/plasma phase from the cellular phase and consequently requires the use of a centrifuge or filtration system. Latex agglutination assays are described in Merskey, et al., Proc. Soc. Exp. Biol. Med. (1969), 131, 871; Castelon, et al., J. Clin. Pathol. (1968), 21, 638; and Singer & Poltz Am. J. Med. [1956 (Dec)], 888.

Both direct and indirect agglutination immunoassays are well known in the art. In these assays, the agglutination of particles to which antigen or antibody is bound is used to indicate the presence or absence of the corresponding antibody or antigen. A variety of particles, including particles of latex, charcoal, kaolinite, or bentonite, as well as both microbial and red blood cells, have been used as agglutinatable carriers. See Mochida, U.S. Pat. No. 4,308,026. The use of erythrocytes as indicator particles is strongly criticized by Patel, U.S. Pat. No. 3,882,225, who says that it is difficult to standardize indicator erythrocytes.

Molinaro, U.S. Pat. No. 4,130,634 describes an assay for an antigen which employs antibody-coated red blood cells. Molinaro emphasizes that the method used to couple the antibody to the erythrocyte must not destroy the reactivity of the antibody. He makes it clear that antibodies which are specific for the erythrocyte are not useful for his assay. He does mention, however, the possibility of using a hybrid antibody with one binding site specific for the antigen and the other specific for the red blood cell.

Chang, U.S. Pat. No. 4,433,059 discloses an agglutination immunoassay reagent in which two antibodies are covalently linked "tail-to-tail", i.e., so as not to alter their specificity. One antibody is specific for an antigen borne by an indicator substance, such as an erythrocyte. This antibody is preferably univalent to avoid nonspecific agglutination. The other antibody is divalent and is specific for the analyte. In preparation for the assay, fresh erythrocytes are coated with the conjugate. The double antibody conjugate-coated RBCs are then incubated with the test serum. Chang does not contemplate the assaying of whole blood samples using a non-autoagglutinating anti-RBC antibody and endogenous erythrocytes.

Chu, U.S. Pat. No. 4,493,793 discloses the construction of a lectin-antibody or lectin-antigen covalently coupled conjugate. His Table I (incorporated by reference) sets forth the carbohydrate specificities of several lectins. He does not teach coupling such a conjugate to an erythrocyte through either the lectin or the antibody receptor.

Other "tail-to-tail" immunological conjugates are known. Segal, U.S. Pat. No. 4,676,980 sets forth the construction of a "tail-to-tail" conjugate of a target cell surface antigen-specific antibody and of a cytotoxic effector cell receptor-specific antibody. Several cross-linking methods, incorporated by reference, are described. This conjugate is intended for use in immunotherapy, in that it will cause the cellular immune system of the patient to lyse the target cell. The target cell would not, of course, be an erythrocyte endogenous to the host.

Li, U.S. Pat. No. 4,661,444 suggests the production of a tail-to-tail conjugate of an analyte-binding antibody and of an antibody specific for the idiotype of the first antibody. This conjugate was to be used in conjunction with an insolubilized analyte-binding antibody in an immunoassay.

Wardlaw, U.S. Pat. No. 4,695,553 teaches use of a monoclonal antibody against a universal erythrocyte antigen as a RBC agglutinating agent to clarify the interface between red blood cells and white blood cells in centrifuged whole blood. He prefers use of antibodies against glycophorin or against H antigen, but also mentions the possibility of using a mixture of lectins. Guesdon, U.S. Pat. No. 4,668,637 discusses the use of antired blood cell antibodies or of lectins for the purpose of erythroadsorption. Bigbee, Molecular Immunology, 20: 1353–1362 (1983) describes the production and testing of four monoclonal antibodies against glycophorin A. The general concept of using in an immunoassay an antibody which reacts with an antigenic determinant shared among all members of a class of analytes of interest (microorganisms) is set forth in McLaughlin, U.S. Pat. No. 4,683,196.

A number of patents deal with antibodies useful in blood typing. See, e.g., Lloyd, U.S. Pat. No. 4,678,747; Graham, Jr., U.S. Pat. No. 4,358,436; Liu, U.S. Pat. No. 4,550,017; Steplewski, U.S. Pat. No. 4,607,009; Lennox, WO83/03477. These antibodies are useful for blood typing because they bind to antigens found only in certain blood cell populations, while for the purpose of this invention, it is desirable to use antibodies (or mixtures thereof) which bind to essentially all erythrocytes.

Zuk, U.S. Pat. No. 4,594,327 recognizes the desirability of performing an immunoassay directly on whole blood samples. In his method, the sample is contacted with both an insolubilized, analyte-specific immunoreagent and with a red blood cell binding agent such as a RBC-specific antibody or a lectin. The analyte-specific immunoreagent and the RBC binding agent are not coupled together, and the assay disclosed is not an agglutination assay.

The problem, in an agglutination immunoassay, of nonspecific agglutination of erythrocytes by anti-erythrocyte antibodies endogenous to the blood sample, was noted by Czismas, U.S. Pat. No. 3,639,558. He proposed eliminating all naturally occurring antigenic sites on the particle by coating the particle with protein.

Theofilopoulos, U.S. Pat. No. 4,342,566; Duermeyer, U.S. Pat. No. 4,292,403 and Goldenberg, U.S. Pat. No. 4,331,647 are of interest as demonstrating the use of specific binding fragments of antibodies as substitutes for intact antibodies in assays. The construction of heterobifunctional antibodies is taught by Auditore-Hargreaves, U.S. Pat. No. 4,446,233; Paulus, U.S. Pat. No. 4,444,878; and Reading, U.S. Pat. No. 4,474,893. Mochida, U.S. Pat. No. 4,200,436 discloses the use of monovalent antibodies or binding fragments thereof in certain immunoassays. Forrest, U.S. Pat. No. 4,659,878 mentions that monovalent antibodies cannot form dimers or more extensive complexes with the antigen; such aggregates were said to be capable of interfering with the binding of the antigenantibody complex to a solid phase support.

SUMMARY OF THE INVENTION

The present inventors recognized that there was a need for a method which can be used in the laboratory and in the field, particularly in Third World Countries where there is lack of medical testing facilities for analysis of different types of analytes in whole blood. As indicated above, earlier methods require separation of the blood cells from serum or plasma and are therefore difficult and in many cases impossible to implement in the field.

If erythrocyte-binding molecules are coupled to specific analyte-binding molecules, then the resulting conjugate could be used to bind both endoqenous erythrocytes, and analytes present in a blood ample. The present invention results from the finding that when such a complex is exposed to a blood sample, agglutination of the erythrocytes endogenous to that samples will serve as an indicator of the presence of the relevant analyte (usually, an antigen or antibody) due to cross linking of erythrocytes with the analyte.

ADVANTAGES OF ENDOGENOUS RBC'S (i) Simplifies current assay procedures no need to centrifuge sample; whole blood, collected in the presence of a suitable anticoagulant, is used instead of serum or plasma.

for samples from patients with infectious diseases, such as AIDS or hepatitis, there is minimal sample handling.

appropriate for mass screening programs as conducted by the World Health Organization in third world countries, whose facilities are limited.

the assay is very robust; there is only a single reagent, which is stable in the presence of a bacteriostatic agent such as 0.01% (w/v) sodium azide.

can be used as a field test by veterinary practitioners, when the appropriate animal red cells are used for immunization to produce species specific MAb.

the test is very fast—agglutination occurs in less than three minutes.

the method can be used to monitor therapeutic drugs and patient compliance.

it also has possible use as an OTC self testing assay.

the only equipment needed is a mixing stick, glass or plastic slide, lancet and possibly a microcapillary.

(ii) Advantages over exogenous erythrocytes include:

no pretreatment of erythrocytes. U.S. Pat. No. 4,433,059 uses blood group 0 negative cells, which have been spun down, reacted with antibody conjugate for 15–30 minutes and washed 3x in PBS. U.S. Pat. No. 4,668,647 uses sheep red blood cells, which had been washed and resuspended in PBS. After the reaction, which takes place on a solid support, the cells are then fixed.

no pretreatment of samples. U.S. Pat. No. 4,433,059 notes that samples have to be heat inactivated to avoid interference due to complement. Rabbit serum and bovine albumin must also be added to minimize other non-specific reactions. None of this is necessary with the present system, where undiluted whole blood from patients may be reacted directly with reagent. This reagent contains unrelated monoclonal antibody to prevent any human anti-mouse reactions, which may occur.

Thus, it is possible to dispense with the cumbersome separation of cells from serum and with the sensitization and fixing of exogenous erythrocytes intended for use as indicator particles in agglutination assays. The endogenous erythrocytes are sensitized by the conjugate.

Another novel aspect of applicants' agglutination reagents and assays is the selection of an erythrocyte binding molecule such that incubation of conjugate with endogenous erythrocytes will not cause agglutination of the erythrocytes unless analyte is also present—such erythrocyte binding molecules are termed herein "non-autoagglutinating."

The erythrocyte binding molecule is preferably a monoclonal antibody and especially an anti-glycophorin antibody. It is believed that this antibody is non-autoagglutinating for steric reasons; either the binding sites of the intact antibody are able only to bind adjacent epitopes on the same erythrocyte or only one of the two binding sites can bind to glycophorin at one time.

Applicant's assay can detect small antigens without repeating determinants, using two conjugates, one bearing an analyte-specific binding molecule and the other, a binding molecule specific for a new epitope formed by the binding of the first conjugate to the analyte. This allows crosslinking in the presence of the antigen to be measured.

DETAILED DESCRIPTION OF THE INVENTION

Figure 1:
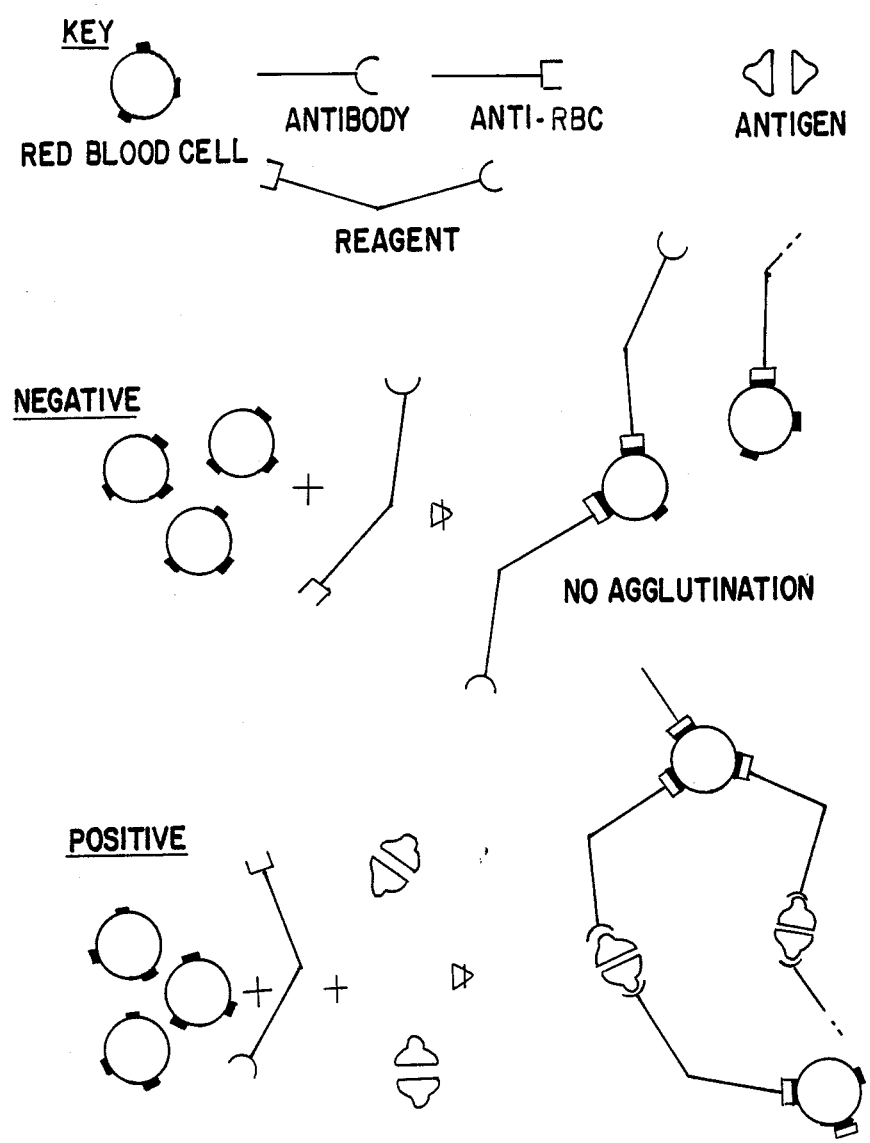
FIG. 1 is a schematic representation of erythrocytes showing positive and negative agglutination results with antibody complexes in the presence and absence of antigen respectively.
Figure 2:
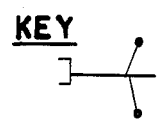
FIG. 2. is a schematic representation of erythrocytes showing positive and negative agglutination results with a complex of antibody and an antigen in the presence and absence, respectively of anti-antigen antibodies.
Figure 2:
Figure 2:
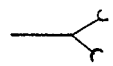
Figure 2:
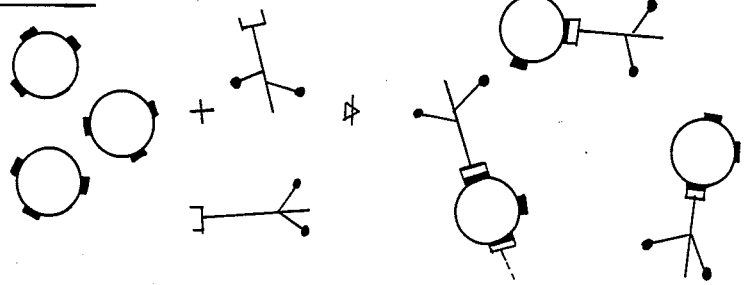
Figure 2:
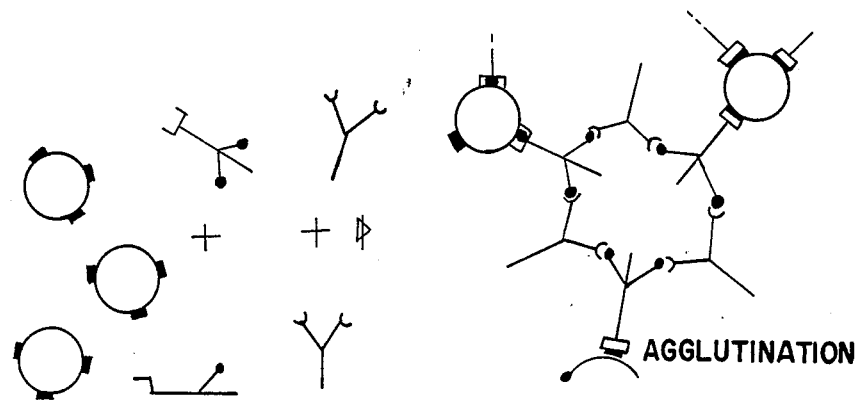
Figure 3:
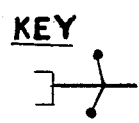
FIG. 3. is a schematic representation depicting (a) erythrocyte agglutination and (b) inhibition of erythrocyte agglutination due to presence of analyte or antigen.
Figure 3:
Figure 3:
Figure 3:
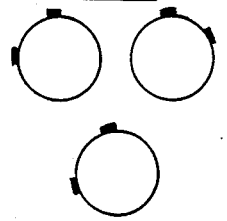
Figure 3:
Figure 3:
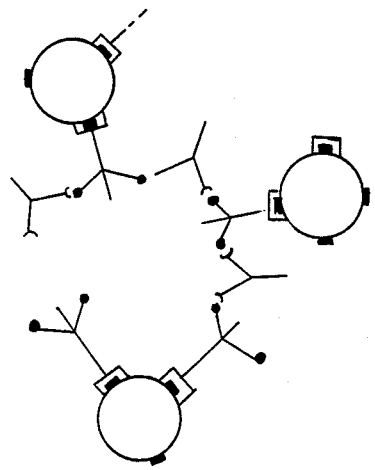
Figure 3:
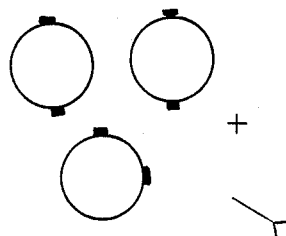
Figure 3:
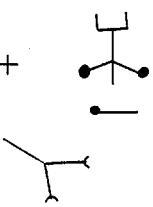
Figure 3:
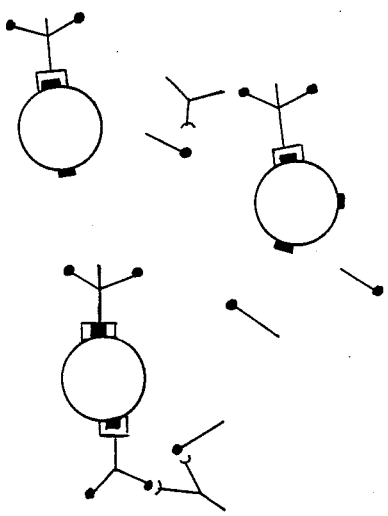
Figure 4:
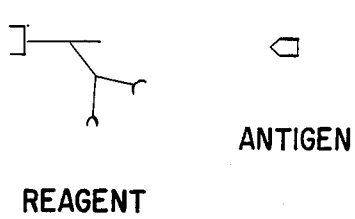
FIG. 4. is a schematic representation depicting mechanisms of agglutination/non-agglutination in connection with an overlapping antigen assay.
Figure 4:
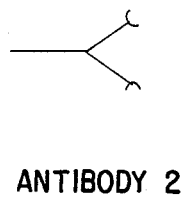
Figure 4:
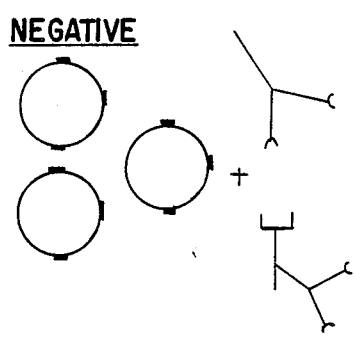
Figure 4:
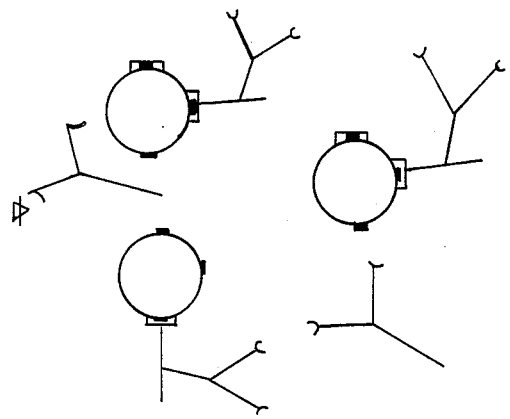
Figure 4:
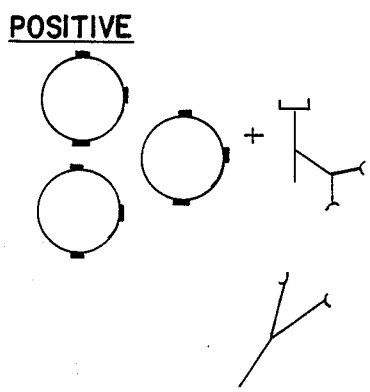
Figure 4:
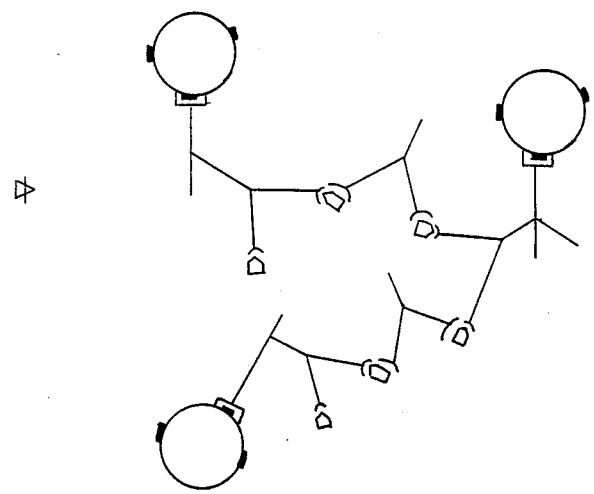

In the agglutination assay of this invention, a reagent is provided which comprises a conjugate comprising at least one erythrocyte binding molecule is coupled to at least one analyte binding molecule, without substantially changing the binding characteristics of either molecule. The conjugate is preferably non-agglutinating when incubated with endogenous erythrocytes in the absence of the analyte.

Erythrocyte Binding Molecules

Erythrocyte membranes contain various antigenic surface constituents, including proteins, glycoproteins, glycolipids and lipoproteins. Antibodies which recognize these constituents may be prepared by conventional techniques using the membrane, or the purified constituents thereof, as immunogens. These antibodies may be monoclonal or polyclonal in nature. Either the intact antibody, or specific binding fragments thereof, may be used as erythrocyte binding molecules (EBM). The antibody or antibody fragment may be divalent or univalent.

In addition, glycoproteins, glycolipids and other carbohydrate structures on the surface of erythrocytes are recognized by chemicals known as lectins, which have an affinity for carbohydrates. These lectins may also be used as EBMs. Other receptor molecules with specific affinity for the erythrocyte surface also may be used.

The preferred EBMs of the present invention will recognize erythrocyte membrane constituents found on all, or nearly all erythrocytes, so that erythrocytes endogenous to the blood sample may be used as the agglutinating particles. Such constituents include the so-called "public antigens."

Erythrocyte membranes are lipid bilayers with a variety of proteins either on the surface or with a hydrophobic portion allowing the protein to anchor in or pass through the membrane, and may have part of the molecule inside the cell. Glycophorin A is an example of a molecule which traverses the cell membrane. The blood group specificity is conferred by carbohydrate or glycolipid moieties, which are attached to membrane proteins. It is thus important that an EBM should recognize either the protein part of a membrane glycoprotein constituent, which is common to all erythrocytes of a particular species or another common structure. The ability of a bivalent EBM to agglutinate red cells will depend on steric factors, such as the mobility of the molecule and the position of the binding site above the lipid bilayer.

The proteins of erythrocyte membranes include: glycophorin A (MN, $En^a$, $Wr^b$), glycophorin B (Ss, 'N', U) and the minor constituents, integral membrane protein 1 (Rhesus), membrane attached glycoprotein C4 (Chido & Rodgers), integral membrane glycoprotein (anion channel), glycolipids (Lewis), glycosphingolipids (ABH, li, P, Tk), ankyrin, spectrin, protein 4-1, F-actin. [The associated blood group factors are in parentheses.]

The following publications are incorporated by reference:

1. The red cell membrane. S. B. Shohet & E. Beutler, in: Hematology, 3rd ed. Eds: Williams, Beutler, Erslev & Lichtman, 1983. (Review of all erythrocyte membrane antigens)
2. The red cell membrane skeleton. V. T. Marchesi. Blood, 61, 1-11, 1983. (Review of the skeleton proteins)

An especially preferred EBM is one recognizing glycophorin. When erythrocyte sialoglycopeptides are extracted from membranes, the main fraction (approximately 75% of total) is glycophorin. This molecule comprises 131 amino acids with 16 oligosaccharide chains. Thus, this is an abundant moiety, which could allow antibody attachment without agglutinating the red cells. It is also readily available in a relatively pure form commercially, e.g., from Sigma Chemical Company. (See "Fractionation of the Major Sialoglycopeptides of the Human Red Blood Cell Membrane" H. Furthmayr, M. Tomita & V. T. Marchesi. BBRC 65, 1975, 113-122).

When the erythrocyte binding molecule is multivalent, as in the case of a normal antibody, it is desirable that the molecule recognize an erythrocyte membrane constituent which is abundant and well-distributed, and the binding site should be in such a position that crosslinking between cells is inhibited by steric hindrance, thereby avoiding premature red cell agglutination.

It is preferable, but not necessary, that a single EBM be used that recognizes essentially all erythrocytes. Several EBMs may be used, either in the same or in separate conjugates, each of which recognizes a particular group of erythrocytes, but which in aggregate recognize essentially all erythrocytes.

While it is preferable that the EBM recognize a natural surface constituent of the erythrocyte, it is possible to coat erythrocytes with a ligand recognized by the EBM, or to treat the erythrocytes so as to expose a normally cryptic ligand.

Analytes

This invention is not limited to the detection of any particular analyte. The analyte may be a substance normally found in blood, such as a blood protein or a hormone, or it may be a foreign substance, such as a drug (including both therapeutic drugs and drugs of abuse), or an organism, such as a virus (by recognizing a virus coat protein) bacterium, protozoan, fungus, or multicellular parasite (e.g., heartworm).

The analyte may have repeating epitopes, recognizable by one analyte binding molecule, or unique epitopes, where a mixture of analyte binding molecules is necessary. However, analytes which can only be bound by one ABM at a time, may also be detected.

Analyte Binding Molecule

The analyte binding molecule may be any substance having a preferential affinity for the analyte, including monoclonal or polyclonal antibodies lectins, enzymes, or other binding proteins or substances (or binding fragments thereof). Where the analyte is an antigen, the ABM is usually an antibody. Where the analyte is an antibody, the ABM is usually an antigen recognized by that antibody. When the analyte to be detected has no repeating epitopes, two or more ABMs are required with different specificities for the analyte. The reagent in this case will be either a mixture of EBM bound to ABM 1 and EBM bound to ABM 2, or EBM with both ABMs attached.

The analyte binding molecule need not bind the analyte directly. For example, in an assay for thyroxine, one ABM may be directed against a thyroxine binding protein if the latter is known to be present in the sample, or is separately provided.

Coupling of EBM and ABM

The EBM and the ABM may be coupled together directly or indirectly, and by covalent or non-covalent means (or a combination thereof). Where multiple EBMs or ABMs are used, EBMs or ABMs may be coupled together, with one or more ABMs coupled directly to an EBM. The following table summarizes some of the covalent coupling methods known in the art.

Heterobifunctional

1. SPDP
   (N-Succinimidyl 3-2 (pyridyldithio)propionate)
   Neurath, et al., 1981, J. Virol., Meth., 3, 155-165.
2. MBS
   (m-maleimidobenzoyl-N-hydroxysuocinimide ester)
   Kitagaw, et al., 1976, J. Biochem., 79, 223-236.
3. SIAB
   (N-succinimidyl-4-iodoacetylaminobenzoate) Weltman, et al., 1983, Bio. Techniques, 1, 148-152.

Selective Bifunctional

P-isothiocyanatobenzoylchloride U.S. Pat. No. 4 680 338

Bifunctional

1. BSOCOES
   Bis[2-(succinimidooxycarbonyloxy>ethyllsulphate
   Zarling, et al., 1980, J. Immunol., 124, 913-920.
2. BS
   Bis(sulphosuccinimidyl)suberate Staros, 1982, Biochemistry, 21, 3950-3955.

Other

1. Glutaraldehyde
   Avrameas, 1969, Immunochem., 6, 43.
2. Periodate Oxidization
   Nakane and Kawoi, 1974, J. Histochem. Cytochem., 22, 1084-1091.
3. Carbodimide Of the foregoing methods of covalent coupling, conjugation with SPDP is preferred.

The EBM and the ABM may also be coupled non-covalently, for example, by (a) attaching biotin to one and avidin (or strepavidin) to the other), (b) attaching an anti-antibody to one, which then binds the other, (c) attaching protein A to one, which then binds the $F_c$ portion of the other, and (d) attaching a sugar to one and a corresponding lectin to the other.

It should be understood that in coupling the EBM and the ABM, the binding characteristics should be changed as little as possible. To avoid adverse effects on binding, the Fc portions ("tails") of antibodies are usually coupled. Also, it may be advantageous to provide a spacer moiety between the EBM and the ABM to reduce steric hindrance.

The EBM/ABM conjugate may be a chimeric antibody. One method of constructing such a conjugate is the following:

(a) preparing F(ab)$_2$ fragments of a selected antibody by pepsin digestion;
(b) reducing and treating the fragments with Ellman's reagent to produce Fab fragments of the selected antibody;
(c) thiolysing a selected specific antibody or a selected erythrocyte antibody; and
(d) coupling the thioylated Fab fragment to the Ellman's reagent treated Fab fragment to produce a chimeric anti-erythrocyte antibody-antigen specific antibody conjugate.

Another method is set forth below:
(a) treating an anti-erythrocyte monoclonal antibody-producing hybridoma and an antigen specific monoclonal antibody-producing hybridoma with a distinct site-specific irreversible inhibitor of macromolecular biosynthesis;
(b) fusing the two different monoclonal antibody-producing hybridomas with polyethylene glycol;
(c) cloning the fused cells either in soft agarose or by limiting dilution;
(d) selecting cloned heterohybridomas secreting chimeric anti-erythrocyte antibody-antigen specific antibody with a screening assay appropriate to the antibodies.

Preferably the inhibitor is selected from the group consisting of emetine, actinomycin D, hydroxyurea, ouabain, cycloheximide, edine and sparsomycin.

The chimeric antibody may be two half-molecules, one with specificity for erythrocytes (the EBM) and the other with specificity for the analyte (the ABM). In this case the disulfide bonds of the antibody couple the ABM to the EBM to form the conjugate. Alternatively, the two half-molecules may be specific for the same or different epitopes of the analyte. In this second case, the chimeric antibody is really two ABMs and must be coupled to an EBM to form a tripartite conjugate. Tripartite conjugates may be formed by other means, such as attaching the EBM and two ABMs to a macromolecular spacer.

The simplest agglutination reagent contemplated is one comprising a single conjugate of one EBM to one ABM. This reagent is suitable for the detection of antigens with repeating epitopes.

Antigenic analytes large enough to allow simultaneous binding of two antibody molecules, but which lack repeating epitopes, are known. They include many peptide and protein hormones. For agglutination to occur, the antigen must interact with the reagent so that at least some molecules of antigen act as a bridge between proximate erythrocytes. For assaying such analytes, it is preferably to employ a reagent comprising two or more distinct conjugates, i.e., ABM1/EBM+ABM2/EBM where AMB1 and ABM2 bind to different, non-overlapping epitopes of the analyte. One might instead use a more complex single conjugate, ABM1/ABM2/EBM, where the stereochemistry is unlikely to favor the binding of both ABMs on the same conjugate molecule to the same analyte molecule.

Erythrocyte Agglutination Assay

Both direct and indirect agglutination assays are known in the art. In the conventional direct assay for an antigen, red cells are coated with antibody, and reacted with the sample. Multifunctional antigens act as bridges between the coated red blood cells, creating an agglutinate. In the conventional indirect assay, red cells are coated with antigen, and contacted with both a soluble antibody and with sample. Sample antigen competitively inhibits the binding of the sensitized red cells by the antibody, and hence the agglutination. It is also possible to additionally use an antibody - sensitized RBC. See Mochida, U.S. Pat. No. 4,308,026.

The reagent of the present invention may be used in either a direct or an indirect agglutination assay format. However, unlike conventional assays, it is not necessary to precoat erythrocytes with antibody or antigen. Rather, the reagent may be added to a blood sample containing endogenous erythrocytes, whereupon it will sensitize the cells, rendering them able to bind sample analyte (a direct assay) or to compete with sample analyte for a soluble analyte-binding molecule analyte-binding molecule (an indirect assay).

For some small circulating molecules such as synthetic or natural steriods, i.d., digoxin, theophylline, etc., or drugs of abuse, i.e., phenobarbital, cannabinoids, opioids, etc.,the analyte in question may be too small to provide the two necessary antigenic epitopes for antibody binding (or other "epitopes" for recognition by other binding molecules) to allow cross-linking and subsequent erythrocyte agglutination.

For the assay of small molecules, as in drug monitoring or indeed for any other antigens, an agglutination inhibition assay is preferred. In this case, a two stage test is expected. The first stage would be addition of a reagent consisting of the analyte or analyte analogue coupled to the non-agglutinating EBM, and the second stage would be addition of an unconjugated ABM. (The two stages may be reversed). If analyte is present in the blood sample, the specific binding of the ABM to the EBM-analyte analogue conjugate will be inhibited, leading to a loss of agglutination. Otherwise, agglutination occurs.

The term "analyte analogue" includes both the analyte, and any substance also specifically bound by the ABM when such binding is competively inhibited by the analyte. The analyte analogue may be anti-idiotypic antibody raised against the antigen-binding site of an analyte-binding antibody.

For the detection of such small molecules by direct agglutination assay, at least two specific monoclonal antibodies could be used. One monoclonal antibody which is capable of binding directly to the small circulating antigen would be coupled to the erythrocyte binding molecule. The second (secondary) monoclonal antibody would be incubated with the above conjugate and the analyte and would be capable of binding to a new antigenic determinant comprised of an overlapping region of the first monoclonal antibody and the antigen that exists only when the first monoclonal antibody binds antigen. Thus, the second monoclonal antibody acts as the erythrocyte "bridge," finally causes cross-linking between different red cells allowing agglutination to occur. This method, of course, is not restricted to monoepitopic analytes.

For stereochemical reasons, it may be difficult for a single secondary antibody molecule to bind simultaneously to two conjugate: analyte complexes. Thus, it may be preferable to conjugate the secondary antibody with an erythrocyte binding molecule.

In stating that a sample is to be incubated with a plurality of reagents it is to be understood that the contact may be simultaneous or sequential, without limitation to any particular order or duration of contact.

EXAMPLE 1

Comparative testing of blood samples was by means of ELISA for the purpose of confirming positives and negatives obtained with the erythrocyte assay.

Control blood samples comprised ELISA negative blood samples and ELISA positive samples from infected patients.

Immunization and Screening Procedure

Mice were immunized with human red blood cells and monoclonal antibodies produced by fusing the spleen cells of immunized animals with mouse myeloma cells. The antibodies were screened by both spin agglutination assay and enzyme immunoassay, where glycophorin was bound to a microtitre plate. Spin agglutination was performed by a modification of Wyatt & Street, Aust. J. Med. Lab. Sci, 4 48–50. 50 ul of cell culture supernatant was mixed with 50 ul of a 1% red blood cell suspension in a microtitre plate. For this example, antibodies which bound glycophorin, but did not agglutinate, were selected. The reaction of monoclonal antibody and glycophorin was determined by enzyme immunoassay. Microplates were coated with 10 micrograms/ml human glycophorin [Sigma Cat. No. G 7389] and washed, then incubated with serial dilutions of monoclonal antibody. After further washing, the presence of bound antibody was determined by the addition of enzyme labelled anti-mouse antibodies followed by the addition of substrate. The titre was determined to the largest dilution of monoclonal, which gave an A420 reading greater than 0.1 OD units above background.

Of 384 wells, 40 primary clones were chosen. These gave either a positive spin agglutination assay, a response to glycophorin on EIA or both.

| EIA | Spin agglutination | Number of clones |
| --- | --- | --- |
| Negative | Positive | 4 |
| Positive | Positive | 20 |
| Positive | Negative | 16 |

Subsequent absorption studies were performed to confirm that the antibodies recognized a glycophorin domain exposed on the red cell surface.

The results of the screening assays on ascitic fluid are listed below:

| | Ascitic Fluid Titre | | Red Cell |
| --- | --- | --- | --- |
| Clone | Spin Agglutination | Glycophorin EIA | Absorption Test |
| RAT 1D3/167 | 512000 | <1000 | Positive |
| RAT 3D6/5 | 6400 | 1024000 | Positive |
| RAT 1C3/86 | <1000 | 1024000 | Positive |
| RAT 3B1/172 | 256000 | 2000 | Positive |
| RAT 3D3/22 | 4000 | 1024000 | Positive |
| RAT 3D5/61 | 128000 | 1024000 | Positive |
| RAT 1A2/187 | <1000 | 256000 | Positive |
| RAT 2A2/187 | <1000 | 128000 | Positive |
| RAT 1A3/129 | <1000 | 128000 | Weak |
| RAT 1C4/5 | <1000 | 128000 | Positive |
| RAT 4C3/13 | <1000 | 128000 | Positive |
| RAT 3B1/70 | <1000 | 517000 | Positive |

Purification of RAT 1C3/86

Monoclonal antibodies were purified to homogeneity from ascitic fluids by chromatography on hydroxylapatite (Stanker, et al., J. Immunol. Methods 76, 157, 1985).

PREPARATION OF PEPTIDE-AB CONJUGATE

1. SPDP labeling of the erythrocyte binding Ab (RAT 1C3/86)

To 0.25 ml of 13.8 mg/ml RAT 1C3/86 was added 12.5 ul of 2 mg/ml SPDP in dimethyl formamide and the reaction was allowed to proceed for 1 hour at 25° C. Unreacted SPDP was removed by gel filtration on Sephadex G 25 and the level of SPDP labelling (1.4 moles/mole) was determined.

2. Reduction of peptide 3.2

Peptide 3.2 (sequence RILAVERYLKDQQLLGWGCSGK, corresponding to residues 579–601 of the major coat protein of HIV 1) was dissolved in 1 ml of 100 mM Tris HCL, 1 mM EDTA pH 8.0 and reacted with 10 ul of 2 mercaptoethanol for 45 minutes at 40° C. The reaction was terminated by the addition of 4 drops of trifluoroacetic acid (TFA) and 1 ml of aqueous 0.1% TFA. The mixture was applied to a Sep-pak (Waters) C 18 cartridge that had been treated with 20 ml of 60% acetonitrile. 0.1% TFA and equilibrated with 0.1% TFA. The reduced peptide was cycled through the Sep-pak twice before washing with 20 ml 0.1% TFA. The reduced peptide was eluted from the Sep-pak with 2×2 ml of 60% acetonitrile, 0.1% TFA. The sample was rotary evaporated to dryness prior to coupling.

3. Conjugation

The peptide was dissolved in 0.2 ml of a buffer containing 100 mM potassium phosphate, 100 mM sodium chloride and 4 M guanidine HCl pH 7.4 and mixed with 2.2 mg of SPDP of labelled antibody in the same buffer, but without guanidine HCl. The flask was incubated overnight at 25° C.

4. Gel Filtration Chromatography

Unreacted peptide and SPDP by-products were removed by gel filtration on a Superose 6 column (Pharmacia) in phosphate buffered saline and antibody containing fractions were pooled and stored at 4° C. after addition of 0.01% sodium azide as a preservative.

5. Preparation of reagent for assay

Two volumes of conjugates were mixed with one volume of a 10 mg/ml solution of an unrelated monoclonal antibody (Bruce 5) prepared as described in Bundesen, et al., Vet. Immun., Immunopath. 8, 245–260, 1985.

Assay procedure

For assay, 10 ul of heparinized whole blood was placed on a glass slide. 30 ul of reagent was added and mixed. The slide was rocked for up to three minutes and the presence or absence of agglutination noted.

EXAMPLE 2

Preparation of Chimeric Antibodies

Monoclonal antibodies RAT 1C3/86 (anti-human red blood cell) and DD-1C3/108 (anti-human D-dimer as described by Rylatt, et al., 1983, Thrombosis Res., 31, 767–778) were digested with pepsin essentially as described by Hackman, et al., 1981, Immunology, 15, 429–436, and purified by chromotrography on a TSK-3000 SW column. 2 mg RAT 1C3/86 was digested for 45 minutes with 1% w/w pepsin in a buffer containing 0.1 M acetic acid, 70 mM sodium chloride pH 3.5. Meanwhile, 2 mg DD-1C3/108 was digested with 1% w/w pepsin for 2 hours in the same buffer. The reactions were terminated by the addition of 1.5 M Tris to raise the pH 8. The F(ab)2 fragments were purified by gel filtration chromatography on TSK-3000 SW column.

Reduction of the F(ab)2, and subsequent blocking of the Fab fragment, was carried out as described by Brennan, et al., 1985, Science 229, 81–83. A 3 mg/ml F(ab)2 preparation was treated with 1 mM mercaptoethylamine, in the presence of 10 mM sodium arsenite, for 16 hours at 25°C. The Fab fragments were stabilized by reaction with 5.5'-dithiobis (2-nitrobenzoic acid) (Ellman's reagent) for 3 hours at 25° C. The Fab fragment was then purified by gel filtration chromatography on a TSK-3000 SW column.

The thiol form of DD-1C3/108 was regenerated by reaction with 10 mM mercaptoethylamine for 30 minutes at 25° C. Excess reagent was removed by gel filtration chromatography on a TSK-3000 SW column. A mixture of the thiol DD-1C3/108 and the Ellman's reagent treated RAT-1C3/86 was incubated for 16 hours at 25° C. as described by Brennan, et al. Finally, the chimeric antibody was purified by further gel filtration chromatography on a TSK-3000 SW column.

Preparation of reagent

Two volumes of 0.1 mg/ml chimeric antibody was mixed with one volume of 7.5 mg/ml unrelated monoclonal antibody (Bruce 5).

Assay procedure

For assay, 10 ul of heparinized whole blood was placed on a glass slide. 30 ul of reagent was added and mixed. The slide was rocked for three minutes and in the presence of D-dimer agglutination was observed.

We claim:

1. A direct agglutination assay for the presence of an analyte in a whole blood sample from a subject which comprises contacting a blood sample containing erythrocytes endogenous to the subject with an agglutination reagent which comprises a conjugate of (a) an intact multivalent monoclonal antibody which binds to erythrocyte membranes or a multivalent binding fragment thereof, and (b) an analyte binding molecule, said conjugate being essentially incapable of agglutinating said erythrocytes in the absence of analyte, observing whether the erythrocytes are agglutinated and directly correlating the agglutination with the amount of analyte present; said assay being further characterized in that at no time are the sample or the conjugate with erythrocytes exogenous to the subject.

2. The assay of claim 1 wherein the erythrocyte binding molecule is an antibody for glycophorin or a specific binding fragment thereof.

3. The assay of claim 1 further comprising adding a secondary antibody which binds to a new epitope formed by the binding of the analyte binding molecule to the analyte.

4. An indirect agglutination assay for the presence of an analyte in a whole blood sample from a subject which comprises (a) contacting a blood sample containing erythrocytes endogenous to the subject with (i) an agglutination reagent which comprises a conjugate of (a) an intact multivalent monoclonal antibody which binds to erythrocyte membranes or a multivalent binding fragment thereof, and (b) an analyte analogue, said conjugate being capable of agglutinating erythrocytes but only in the presence of a multivalent analyte binding agent, and (ii) a soluble analyte binding reagent which is essentially incapable of agglutinating erythrocytes, (b) permitting said conjugate to compete with sample analyte for the analyte binding sites of the analyte binding reagent, (c) observing whether agglutination occurs, and (d) inversely correlating the degree of agglutination with the amount of analyte present; said assay further being characterized in that at no time are the sample, the conjugate or the analyte binding reagent contacted with erythrocytex exogenous to the subject.

5. The assay of claim 4 in which the antibody is an anti-glycophorin antibody.

* * * * *